(12) United States Patent
Simmons

(10) Patent No.: US 9,212,206 B1
(45) Date of Patent: Dec. 15, 2015

(54) 4-FLUORO-THIO-CONTAINING INHIBITORS OF APP2, COMPOSITIONS THEREOF AND METHOD OF USE

(71) Applicant: William H Simmons, Westchester, IL (US)

(72) Inventor: William H Simmons, Westchester, IL (US)

( * ) Notice: Subject to any disclaimer, the term of this patent is extended or adjusted under 35 U.S.C. 154(b) by 0 days.

(21) Appl. No.: 14/544,096

(22) Filed: Nov. 24, 2014

(51) Int. Cl.
*A61K 38/06* (2006.01)
*C07K 5/097* (2006.01)
*A61K 38/00* (2006.01)

(52) U.S. Cl.
CPC ............... *C07K 5/0823* (2013.01); *A61K 38/06* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,507,312 A | 3/1985 | Suh et al. | |
| 4,549,992 A | 10/1985 | Suh et al. | |
| 4,684,660 A | 8/1987 | Ondetti et al. | |
| 5,508,272 A | 4/1996 | Robl | |
| 5,656,603 A | 8/1997 | Simmons | |
| 6,777,443 B2 | 8/2004 | Fink | |
| 7,390,789 B2 * | 6/2008 | Simmons | A61K 38/556 514/12.5 |

OTHER PUBLICATIONS

Conformation of cis- and trans-4-Fluoro-L-proline in Aqueous Solution, J. T. Gerig and R. S. McLeod, JACS, 95:17, 5725-5729, Aug. 22, 1973.*
Ferdinandy et al., "Interaction of Risk Factors, Cpmorbities, and Comedications with Ischemia/Reperfusion Injury and Cardi ," Pharmacol. Rev. 66: 1142-1174, Oct. 2014.
Sivaraman et al., "Pharmacologic Therapy That Stimulates Conditioning for Cardiac Ischemic/Reperfusion Injury," J. Cardvasc. Pharmacol Ther., 2014 19(1):83-96.

* cited by examiner

*Primary Examiner* — Karlheinz R Skowronek
*Assistant Examiner* — Joseph Fischer
(74) *Attorney, Agent, or Firm* — Donald J. Pochopien

(57) ABSTRACT

The present invention has multiple aspects. In its first aspect, it is directed to a compound that is a 4(S)-fluoro-thio-tripeptide analog that has the unexpectedly superior property of specifically inhibiting the enzyme, membrane-bound aminopeptidase P2 (APP2), whose natural substrate is bradykinin, but not the enzyme angiotensin converting enzyme (ACE) which also cleaves bradykinin. In its second aspect, the present invention is directed to a pharmaceutical composition comprising the 4(S)-fluoro-thio-tripeptide analog and a pharmaceutically acceptable carrier. In its third aspect, the invention is directed to a method of inhibiting bradykinin degradation in a mammalian patient, comprising administering a therapeutically effective amount of the compound of the invention to a mammalian patient in need of inhibition of bradykinin degradation.

20 Claims, 1 Drawing Sheet

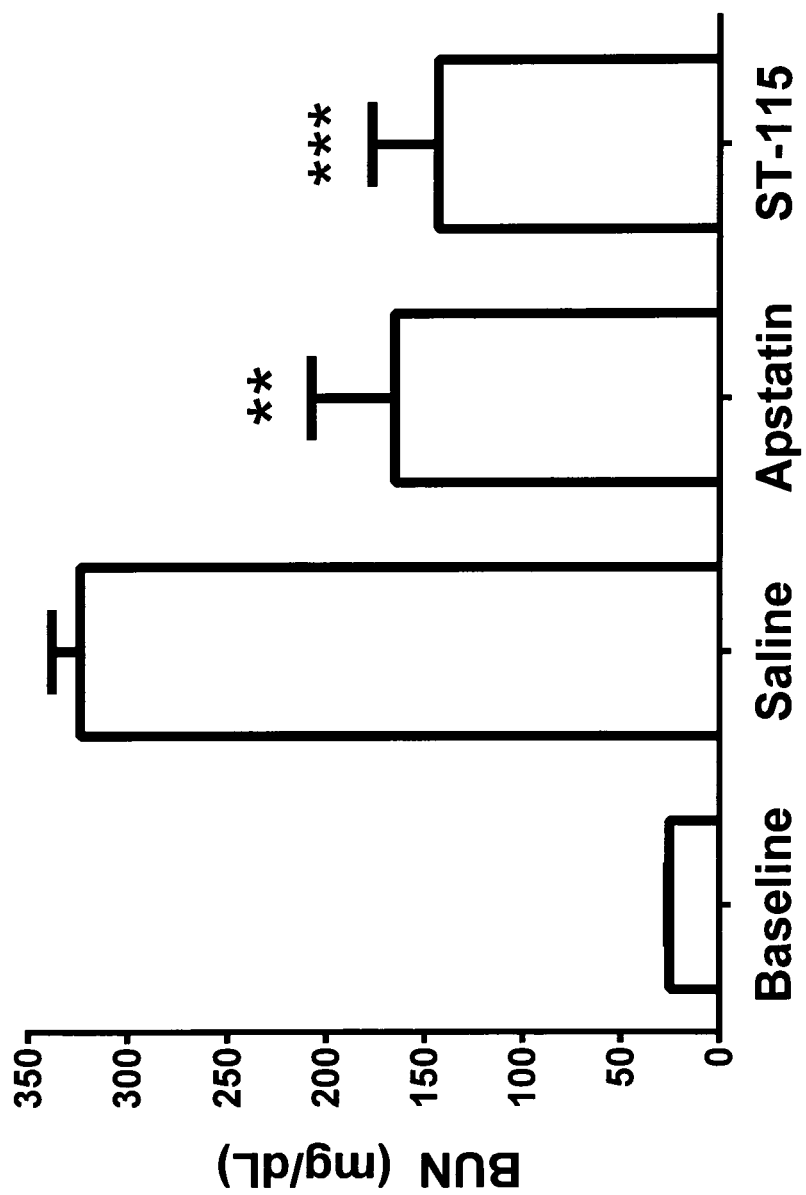

4-FLUORO-THIO-CONTAINING INHIBITORS OF APP2, COMPOSITIONS THEREOF AND METHOD OF USE

BACKGROUND OF THE INVENTION

The present invention is directed to a fluoro-thio-containing compound that is capable of specifically inhibiting the enzyme, membrane-bound aminopeptidase P2 (APP2), whose natural substrate is bradykinin. The compound is useful as a pharmaceutical agent because by inhibiting bradykinin degradation, the compound allows endogenous bradykinin to exert its beneficial effects in the body including dilating coronary arteries, providing protective effects in the heart during myocardial ischemia/reperfusion injury, stimulating formation of new blood vessels, improving organ function in chronic heart and renal disease, and improving glucose tolerance and insulin-sensitivity. The present invention is also directed to a pharmaceutical composition comprising the APP2 inhibitor of the present invention and to a method of inhibiting bradykinin degradation in a mammalian patient, particularly a human patient.

More than a million persons in the U.S. have a myocardial infarction (heart attack) each year, resulting in over 500,000 deaths. "Effective treatment of acute myocardial infarction (MI) is based on procedures that promote the return of blood flow to the ischemic zone of the myocardium, i.e., reperfusion therapy." Ferdinandy et al., "Interaction of Risk Factors, Comorbities, and Comedications with Ischemic/Reperfusion Injury and Cardioprotection by Preconditioning, Postconditioning, and Remote Conditioning," Pharmacol. Rev. 66:1142-1174 at 1144 (October 2014). "Reperfusion, however, may lead to further irreversible myocardial cell death, termed lethal myocardial reperfusion injury." Id. "Currently, there is no effective therapy for combined ischemia/reperfusion injury on the market, and routine pharmacologic agents do not salvage the ischemic/reperfused myocardium." Id. "Therefore, the development of cardioprotective agents to limit the extent of infarcted tissue caused by ischemialreperfusion injury is of great clinical importance." Id. See also Sivaraman, et al., "Pharmacologic Therapy That Simulates Conditioning for Cardiac Ischemic/Reperfusion Injury," J. Cardiovascular Pharm. and Therap., 19(1) 83-96 (2014).

One option for treating ischemic/reperfused myocardium after acute myocardial infarction is to increase the heart's concentration of the nonapeptide hormone, bradykinin, at the time when the heart is being reperfused, i.e., when the blood clot in a heart artery is mechanically removed or dissolved. Although restoration of blood flow to the heart reduces heart damage, it is not as effective as it could be because the rapid increase in flow itself causes a different kind of damage called "reperfusion injury." Bradykinin is known to prevent this kind of injury. However, bradykinin itself is not a good drug because it can seriously lower blood pressure when administered to a patient. Bradykinin is produced in the heart itself during ischemia and reperfusion, but doesn't increase enough to be effective. This is because bradykinin is rapidly degraded by two enzymes: membrane-bound aminopeptidase P2 (APP2) and angiotensin-converting enzyme (ACE) present on blood vessel endothelial cells. Inhibiting APP2 leads to an increase in bradykinin that prevents reperfusion injury. The biochemical mechanisms that cause reperfusion injury and those that prevent it appear to be present in most organs. Therefore, inhibiting APP2 should be protective in most situations where blood flow is stopped for a period of time (ischemia) and then restored (reperfusion). These include, but are not restricted to, ischemia/reperfusion (I/R) of the kidney, brain (stroke), liver, lung, and limb, post-cardiopulmonary bypass surgery, and the whole body I/R such as cardiac arrest and hemorrhagic shock followed by fluid resuscitation. There are currently no approved drugs for preventing reperfusion injury.

The prototype aminopeptidase P inhibitor, apstatin (Formula I), was shown to reduce bradykinin degradation in the isolated perfused rat heart and lung. Apstatin enhanced the blood pressure-lowering effect of intravenously administered bradykinin. In a rat model of

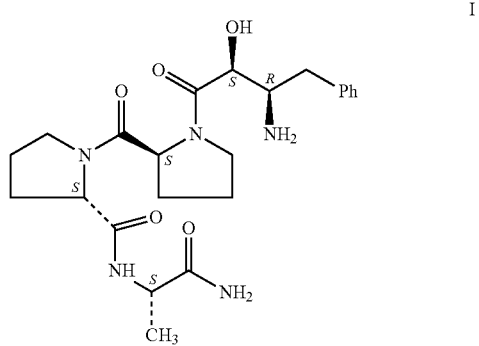

severe hypertension, apstatin, which has no effect by itself, acted synergistically with an ACE inhibitor to reduce blood pressure to normal. [Kitamura et al. "Effects of aminopeptidase P inhibition on kinin-mediated vasodepressor responses," Am. J. Physiol., 276, H1664-H1671 (1999)] APP2 inhibition with apstatin also exhibited cardioprotective effects; in a heart attack model using an isolated perfused heart, apstatin reduced cardiac damage by 74%. [Ersahin et al., "Cardioprotective effects of the aminopeptidase P inhibitor apstatin: studies on ischemia/reperfusion injury in the isolated rat heart," J. Cardiovasc. Pharmacol., 34, 604-611 (1999)] It reduced reperfusion-induced ventricular fibrillation by a similar amount. Subsequent studies in other laboratories showed that inhibiting APP2 by administering apstatin substantially reduced myocardial infarct size in intact rats subjected to regional cardiac ischemia. [Wolfrum et al., "Apstatin, a selective inhibitor of aminopeptidase P, reduces myocardial infarct size by a kinin-dependent pathway," Br. J. Pharmacol., 134, 370-374 (2001); Veeravalli et al., "Infarct size limiting effect of apstatin alone and in combination with enalapril, lisinopril and ramiprilat with experimental myocardial infarction," Pharmacol. Res., 48, 557-563 (2003).] In the later study, apstatin was effective even when administered during ischemia but just before the start of reperfusion. This indicates that apstatin is specifically protecting against reperfusion injury, since it reached the ischemic heart tissue only when reperfusion started.

Apstatin has excellent pharmacological properties and exhibits reasonable potency (micromolar), specificity and metabolic stability. However, it has chemical properties that limit its usefulness as an orally active drug. Although apstatin and related compounds have potential as injectable drugs, the potency and predicted intestinal absorption rate are probably too low to allow them to be effective following oral administration. Oral bioavailability is an essential property when the drug is being used in a chronic situation, such as adjunct treatment for hypertension or chronic heart or kidney disease. Therefore, it is an object of the present invention to discover APP2 inhibitors having greater potency (i.e., a lower $IC_{50}$) than apstatin such that they can be administered in lower dosages as injectable drugs, and/or that because of their potency and chemical structure can be administered in an orally acceptable form.

A novel compound for increasing bradykinin levels is an α-hydroxy, β-amino tripeptide to decapeptide analog, which is disclosed in U.S. Pat. No. 5,656,603 to William H. Simmons, entitled "Aminopeptidase P inhibitors and Uses Thereof."

Another novel compound for increasing bradykinin levels is disclosed in U.S. Pat. No. 7,390,789, entitled "Thio-Containing Inhibitors Of Aminopeptidase P, And Compositions Thereof," which issued to William Simmons on Jun. 24, 2008, and is incorporated herein by reference for its disclosures relating to APP2 (mAPP therein) and ACE inhibitors. The '789 patent discloses various thio-containing tripeptide analogs that in the concentration range of 10 to 3400 nM inhibit purified rat membrane aminopeptidase P by 50% using Arg-Pro-Pro (0.5 mM) as the substrate. However, when these compounds were optimized for metabolic stability and desirable pharmacokinetic properties, they exhibited a loss of target specificity. They also inhibited ACE at concentrations close to the blood levels required to produce a sustained, complete inhibition of APP2.

Current treatment guidelines for acute myocardial infarction state that ACE inhibitors should not be given to patients at the time of reperfusion because of their ability to rapidly decrease blood pressure, primarily by blocking angiotensin II formation. On the other hand, a specific APP2 inhibitor by itself does not decrease blood pressure. Therefore, a compound that inhibits APP2 but not ACE should be safer to use at the time of reperfusion for enhancing the cardioprotective effects of endogenous bradykinin. Accordingly, an object of the present invention is to find a compound that greatly inhibits APP2 while minimally inhibiting ACE

BRIEF SUMMARY OF THE INVENTION

The applicant has discovered a novel 4(S)-fluoro-thio-compound, which is a tripeptide analog that selectively inhibits APP2, but not ACE. This is a desirable feature in treating a reperfusion injury in a mammalian patient because although both APP2 and ACE degrade the same substrate, bradykinin, the inhibition of ACE is also associated with an undesirable drop in blood pressure. Thus, in its first aspect, the present invention is directed to a compound of Formula II:

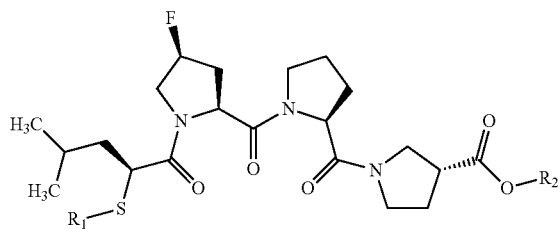

II wherein $R_1$ is H or

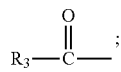

wherein $R_2$ is H; alkyl or substituted alkyl, having from 1 to 6 carbon atoms; or cycloalkyl-$(CH_2)_a$—, aryl-$(CH_2)_a$—, substituted aryl-$(CH_2)_a$—, or heteroaryl-$(CH_2)_a$—, having from 4 to 12 carbon atoms;
wherein $R_3$ is alkyl or substituted alkyl, having 1-6 carbon atoms; or cycloalkyl-$(CH_2)_a$—, aryl-$(CH_2)_a$—, substituted aryl-$(CH_2)_a$—, or heteroaryl-$(CH_2)_a$—, having from 4 to 12 carbon atoms; and
a is zero or an integer from 1 to 6;
or a pharmaceutically acceptable salt thereof.

Preferably, the present invention is directed to a compound of Formula II:
wherein $R_1$ is H, or; $R_3$—(CO)—
wherein $R_2$ is H; or alkyl having from 1 to 6 carbon atoms;
wherein $R_3$ is alkyl having from 1 to 6 carbon atoms;
or a pharmaceutically acceptable salt thereof.

More preferably, the present invention is directed to a compound of Formula II:
wherein $R_1$ is H; and
wherein $R_2$ is H; or alkyl having from 1 to 6 carbon atoms;
or a pharmaceutically acceptable salt thereof.

Most preferably, the present invention is directed to a compound of Formula II:
wherein $R_1$ is H; and $R_2$ is H;
or a pharmaceutically acceptable salt thereof. This compound is referred to herein as ST-115 and also is the compound of Formula III shown below:

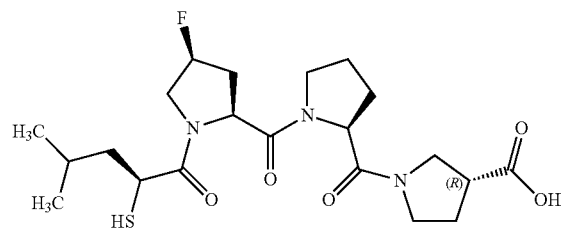

III

In its second aspect, the present invention is directed to a pharmaceutical composition comprising a pharmaceutically acceptable carrier containing a therapeutically effective amount of a compound of Formula II:

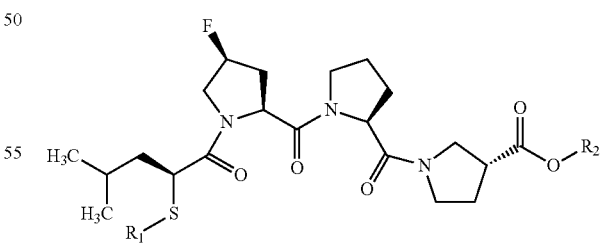

II wherein $R_1$ is H or

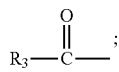

wherein $R_2$ is H; alkyl or substituted alkyl, having from 1 to 6 carbon atoms; or cycloalkyl-$(CH_2)_a$—, aryl-$(CH_2)_a$—, substituted aryl-$(CH_2)_a$—, or heteroaryl-$(CH_2)_a$—, having from 4 to 12 carbon atoms;

wherein $R_3$ is alkyl or substituted alkyl, having 1-6 carbon atoms; or cycloalkyl-$(CH_2)_a$—, aryl-$(CH_2)_a$—, substituted aryl-$(CH_2)_a$—, or heteroaryl-$(CH_2)_a$—, having from 4 to 12 carbon atoms; and a is zero or an integer from 1 to 6;

or a pharmaceutically acceptable salt thereof. More preferred compositions are described in the Detailed Description herein.

In its third aspect, the present invention is directed to a method for inhibiting bradykinin degradation in a mammalian patient, comprising administering to a mammalian patient in need of inhibition of bradykinin degradation a pharmaceutical composition comprising a pharmaceutically acceptable carrier containing a therapeutically effective amount of a compound of Formula II:

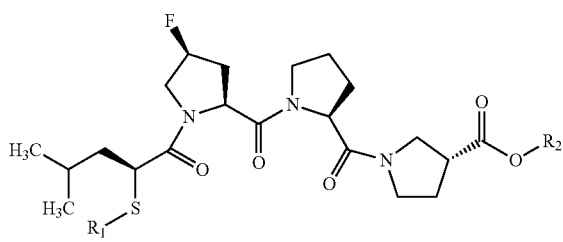

wherein $R_1$ is H or

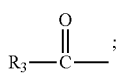

wherein $R_2$ is H; alkyl or substituted alkyl, having from 1 to 6 carbon atoms; or cycloalkyl-$(CH_2)_a$—, aryl-$(CH_2)_a$—, substituted aryl-$(CH_2)_a$—, or heteroaryl-$(CH_2)_a$—, having from 4 to 12 carbon atoms;

wherein $R_3$ is alkyl or substituted alkyl, having 1-6 carbon atoms; or cycloalkyl-$(CH_2)_a$—, aryl-$(CH_2)_a$—, substituted aryl-$(CH_2)_a$—, or heteroaryl-$(CH_2)_a$—, having from 4 to 12 carbon atoms; and a is zero or an integer from 1 to 6;

or a pharmaceutically acceptable salt thereof. Additional methods of the invention, using more preferred compositions are disclosed in the Detailed Description herein.

BRIEF DESCRIPTION OF THE DRAWINGS

FIG. 1 is a bar graph of blood urea nitrogen (BUN) concentrations (y axis) in mg/dL in mice at baseline and after treatment with saline, apstatin or ST-115 (the compound of Formula III) during a created ischemic episode (25 minutes) but 5 minutes before reperfusion was allowed to occur.

DETAILED DESCRIPTION OF THE INVENTION

In its first aspect, the present invention is directed to a compound of Formula II:

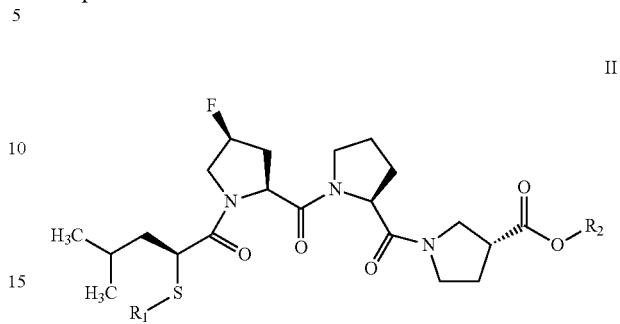

wherein $R_1$ is H or

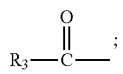

wherein $R_2$ is H; alkyl or substituted alkyl, having from 1 to 6 carbon atoms; or cycloalkyl-$(CH_2)_a$—, aryl-$(CH_2)_a$—, substituted aryl-$(CH_2)_a$—, or heteroaryl-$(CH_2)_a$—, having from 4 to 12 carbon atoms;

wherein $R_3$ is alkyl or substituted alkyl, having from 1 to 6 carbon atoms; or cycloalkyl-$(CH_2)_a$—, aryl-$(CH_2)_a$—, substituted aryl-$(CH_2)_a$—, or heteroaryl-$(CH_2)_a$—, having from 4 to 12 carbon atoms; and a is zero or an integer from 1 to 6;

or a pharmaceutically acceptable salt thereof.

By the term "pharmaceutically acceptable salt," as used herein, refers to relatively non-toxic, inorganic and organic base addition salts of compositions, including without limitation, analgesic agents, therapeutic agents, other materials and the like. Examples of pharmaceutically acceptable salts include those derived from inorganic bases, such as hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, J. Pharm. Sci., 66:1-19 (1977).

By the term "alkyl having from 1 to 6 carbon atoms" is meant to include straight or branched chain carbon atoms. Typical branched chain alkyl have from three to six carbon atoms and include isopropyl, isobutyl, sec-butyl, t-butyl, isopentyl, neopentyl, cyclopentyl, isohexyl, sec-hexyl, 2,2-dimethylbutyl, 3-methylpent-3-yl, cyclohexyl and the like.

In the compound of Formula II, when $R_1$ is $R_3(CO)$—, the sulfur is acylated to its thioester form (—S—(CO)—$R_3$.). As an ester, the compound of Formula II is in its prodrug form. The presence of the free thiol (—SH) is required in order for the compound of Formula II or Formula III to bind to the metal ion at the active site of the enzyme APP2 that it inhibits. The thioester prodrug wouldn't have any APP2 inhibitory activity until it was administered to a patient, where the acyl group would be cleaved off by esterases in the recipient patient's blood or tissues. Administering the compound of the present invention as its prodrug by injection or infusion would insure that there isn't a high concentration of the active drug at the site of injection or infusion. The so-administered prodrug would be diluted and distributed throughout the body before it was activated. One of the reasons why the genus of Formula II has several ester options is that it allows one to control the rate of prodrug activation by choosing an ester that is either rapidly (acetyl) or slowly cleaved by the esterases. The S-acylated prodrug form of the compound of Formula II is also chemically stable for storage, unlike the active drug, which can undergo oxidation of the free sulfhydryl (—SH) to form the disulfide homodimer (which itself would be inactive).

In addition, acylation of both the —SH and the C-terminal carboxyl group produces a diester prodrug of Formula II that is sufficiently hydrophobic that it would be absorbed orally from the GI tract based on pharmacokinetic prediction algorithms. Thus, the diester can be administered to a patient in pill or syrup form. Alternatively, when the diester is administered to a patient by injection or infusion, esterases in the patient's blood or tissue hydrolyze both of the esters, converting the thioester to its active sulfhydryl (—SH) form, and the carboxy ester to its free carboxy form. This thiol carboxy form of the compound of Formula II is the active agent of the present invention, i.e., the potent and highly selective inhibitor of APP2.

One example of a thioester of Formula II or Formula III, is the acetylated thioester, which is the compound of Formula IV herein. The compound of Formula IV was made according to Example 1D herein.

Preferably, the present invention is directed to a compound of Formula II:

wherein $R_1$ is H, or; $R_3$—(CO)— wherein $R_2$ is H; or alkyl having from 1 to 6 carbon atoms;

wherein $R_3$ is alkyl having from 1 to 6 carbon atoms;

or a pharmaceutically acceptable salt thereof.

More preferably, the present invention is directed to a compound of Formula II:

wherein $R_1$ is H; and wherein $R_2$ is H; or alkyl having from 1 to 6 carbon atoms;

or a pharmaceutically acceptable salt thereof.

Most preferably, the present invention is directed to a compound of Formula II:

wherein $R_1$ is H; and $R_2$ is H;

or a pharmaceutically acceptable salt thereof. This compound is also referred to herein as the compound of Formula III as shown below:

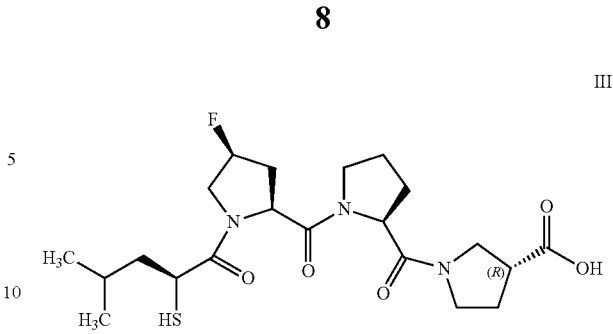

III

In yet another embodiment, the present invention is directed to a compound of Formula II, wherein $R_1$ is $R_3(CO)$—; $R_3$ is methyl; and $R_2$ is H; or a pharmaceutically acceptable salt thereof. This compound is shown in the examples and also referred to herein as the compound of Formula IV:

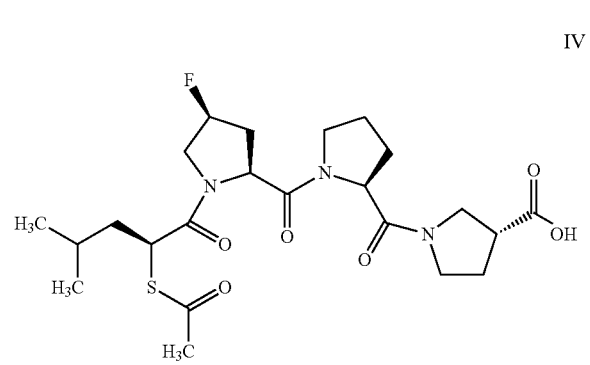 [SMILES: CC(=O)S[C@@H](CC(C)C)C(=O)N1C[C@@H](F)C[C@H]1C(=O)N1CCC[C@H]1C(=O)N1CC[C@@H](C(=O)O)C1]

IV

The compound of the present invention is useful in inhibiting bradykinin because in human model assays, the fluoro analog of Formula III of the present invention was found to selectively inhibit the enzyme human APP2 but not the enzyme human ACE when compared to three non-fluoro peptide analogs (the compounds of Formulas V, VI and VII) of the closest prior art, U.S. Pat. No. 7,390,789 (Simmons). All asymmetric carbon atoms in the compounds of Formulas V, VI and VII are in the S-configuration unless otherwise noted. The methods for determining the APP2 and ACE inhibitory activities of the peptide analogs are described in Examples 2 and 3 herein. The comparative data is reported in Table 1 herein. Specifically, Table 1 compares the chemical structure of each compound tested, its $IC_{50}$ (nM/L) for AAP2, its $IC_{50}$ for ACE and then the compound's ratio of $IC_{50}$s for ACE/AAP2. The compounds were then arranged in descending order in Table 1 based upon their decreasing selectivity as calculated by their $IC_{50}$ ratios for ACE/AAP2.

TABLE 1

| | | Binding affinity ($IC_{50}$ in nanomolar)[1] | | |
| Analog | Structure[3] | APP2 | ACE | ACE/APP2 |
| --- | --- | --- | --- | --- |
| III | ![structure] | 3.7 | 68,000 | 18,000 |

TABLE 1-continued

| Analog | Structure[3] | Binding affinity (IC$_{50}$ in nanomolar)[1] | | |
|---|---|---|---|---|
| | | APP2 | ACE | ACE/APP2 |
| V | | 26 | 49,000 | 1,900 |
| VI | | 9.7 | 12,000 | 1,200 |
| VII | | 3.9 | 640 | 160 |

As disclosed in Table 1, the compound of Formula III of the present invention, having the 4(S)-fluoro, exhibited a superior ability to inhibit human APP2 (IC$_{50}$ of 3.7 nM/L) and a superior inability to inhibit human ACE (IC$_{50}$ of 68,000 nM/L). This is reflected in the compound's IC$_{50}$ ratio for ACE/AAP2 of 18,000. The next best ratio by a comparative compound lacking the 4(S)-fluoro was provided by the prior art compound of Formula V wherein the IC$_{50}$ ratio was 1,900. Comparative compounds of Formulas VI and VII had substantially smaller IC$_{50}$ ratios for ACE/AAP2 of 1,200 and 160, respectively. Since the affinity of the compound of Formula III for APP2 is unexpectedly 18,000-fold higher than that for ACE, it is possible to administer a therapeutic dose of ST-115 that completely inhibits APP2 without having any inhibitory effect on ACE. This property of the compound of Formula III is therefore ideal for a pharmaceutical agent that is to be administered to a myocardial infarct patient at the time of reperfusion to prevent reperfusion injury The compound of Formula III's combined properties of (i) inhibiting APP2 and thus APP2's bradykinin degradation at a low concentration while (ii) selectively not inhibiting ACE even at very high concentrations, was both superior and unexpected over the non 4(S)-fluoro compounds that were tested.

Previous studies have shown that the prototype APP2 inhibitor apstatin can greatly reduce ischemia/reperfusion damage in the heart. FIG. 1 shows that both apstatin and ST-115 (the compound of Formula III) can also reduce ischemia/reperfusion damage in the kidney. In this study, blood flow to both kidneys of the mouse was blocked for 25 min., producing ischemia. Blood flow was then restored (reperfusion). In order to determine the effects of inhibiting APP2 in this model of kidney damage, apstatin, ST-115, or saline (control) were administered intravenously 5 min. before reperfusion. After two days of reperfusion, blood urea nitrogen (BUN, a marker of kidney dysfunction) was measured. In FIG. 1, data are presented as the mean±standard error of the mean. Each drug was separately compared to the control by the unpaired t-test with Welch's correction.  Apstatin vs. Saline, p<0.01; * ST-115 vs. Saline, p<0.001.

FIG. 1 shows that the saline-treated mice had very high BUN values compared to baseline values in mice, indicating major kidney damage. Compared to saline, apstatin reduced BUN by 49%, while ST-115 reduced it by 56%. In addition, 29% of saline control mice died before the prespecified 2-day BUN measurement point, while no apstatin or ST-115 treated mice died early. The fact that apstatin and ST-115 were protective when given just before reperfusion suggest that they are specifically blocking reperfusion damage rather than ischemic damage in this model. Thus, the 4(S)-fluoro compound of Formula III, and the related 4(S)-fluoro compounds of Formula II, would be useful as a pharmaceutical agent in a method for blocking reperfusion injury to tissue in a mammalian patient. In a more preferred embodiment, they would be useful as pharmaceutical agents administered to a mammalian patient in a method for blocking reperfusion injury to the heart or kidney of a mammalian patient.

Apstatin and the compound of Formula III are structurally different molecules that both inhibit APP2. The fact that both had similar protective effects suggest that their mechanism of action is similar, i.e., the inhibition of endogenous APP2. A functional difference between the two is that the compound of Formula III had an effect at a dose that was 180-fold lower than that of apstatin, which is consistent with the large difference in their IC$_{50}$ values for inhibiting APP2 in vitro. The fact that APP2 inhibition can reduce reperfusion damage in both heart and kidney suggests that the mechanisms for both producing and blocking reperfusion damage may be redundant and present in many other, if not all, tissues in the body. Therefore, the 4(S)-fluoro compound of Formula III, and the related 4(S)-fluoro compounds of Formula II should be useful for blocking many types of ischemia/reperfusion injury.

In its second aspect, the present invention is directed to a pharmaceutical composition comprising a pharmaceutically acceptable carrier containing a therapeutically effective amount of a compound of Formula II:

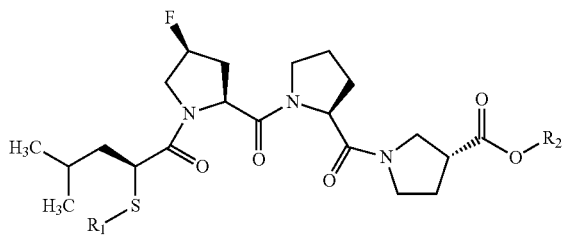

wherein $R_1$ is H or

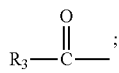

wherein $R_2$ is H; alkyl or substituted alkyl, having from 1 to 6 carbon atoms; or cycloalkyl-$(CH_2)_a$—, aryl-$(CH_2)_a$—, substituted aryl-$(CH_2)_a$—, or heteroaryl-$(CH_2)_a$—, having from 4 to 12 carbon atoms;

wherein $R_3$ is alkyl or substituted alkyl, having 1-6 carbon atoms; or cycloalkyl-$(CH_2)_a$—, aryl-$(CH_2)_a$—, substituted aryl-$(CH_2)_a$—, or heteroaryl-$(CH_2)_a$—, having from 4 to 12 carbon atoms; and a is zero or an integer from 1 to 6;

or a pharmaceutically acceptable salt thereof.

The term "therapeutically effective amount" as used herein means that amount of drug or pharmaceutical agent that will elicit the biological or medical response of a tissue, system or animal that is being sought by a researcher or clinician. An effective but nontoxic quantity of the compound is employed in treatment. The dosage regimen for preventing or treating symptoms by the compounds of this invention is selected in accordance with a variety of factors including the type, age, weight, sex, and medical condition of the mammal, the severity of the symptoms, the route of administration of the particular compound employed. An ordinary skilled physician or veterinarian will readily determine and prescribe the effective amount based on the route of administration of the agent to prevent or arrest the progress of the condition. In so proceeding, the physician or veterinarian employs relatively low dosages at first, subsequently increasing the dose until a maximum response is obtained.

In rats, bradykinin potentiation by apstatin has been observed with 0.08-0.8 mg/kg intravenously when administered over a one hour period. More potent inhibitors of the present invention should be effective at ten- to one hundred eighty-fold lower dosages. See e.g., Table 1. Less potent inhibitors would require a greater dosage to provide the same therapeutic result. A typical therapeutically effective dose of a compound of the present invention is from about 0.0003 mg/kg to 0.8 mg/kg, when given intravenously.

Regardless of the route of administration selected, a nontoxic but therapeutically effective quantity of one or more compounds of this invention is employed in any treatment. For preventing or treating a hypertensive condition or for treating a myocardial ischemia/reperfusion injury with the compounds of this invention, a dosage is selected in accordance with a variety of factors, including the type, age, weight, sex, and medical condition of the patient, the severity of the condition, the route of administration, and the particular compound employed in the treatment. A physician or veterinarian of ordinary skill can readily determine and prescribe the effective amount of the drug required to prevent or arrest the progress of the condition. In so proceeding, the physician or veterinarian could employ relatively low doses at first and subsequently increase the dose until a maximum response is obtained. Daily dosages of the compounds of the invention vary depending upon the $IC_{50}$ of the compound of the invention. However, oral dosages are ordinarily in the range of about 0.1 mg/kg up to about 200 mg/kg, (preferably, in the range of about 2.0 to 84.0 mg/kg (orally)).

The term "pharmaceutically acceptable carrier," as used herein, means a pharmaceutically-acceptable material, composition or vehicle, such as a dispersion or suspension aid, surface active agent, pH modifier, isotonic agent, thickening or emulsifying agent, preservative, solid binder, lubricant and the like, as suited to the particular dosage form desired. Remington: The Science and Practice of Pharmacy, 20th Ed., ed. A. Gennaro, Lippincott Williams & Wilkins, 2000 discloses various carriers used in formulating pharmaceutically acceptable compositions and known techniques for the preparation thereof. Also, Strickley, Pharmaceutical Research, 21(2) 201-230 (2004) reviews pharmaceutically acceptable excipients used in commercial products to solubilize compounds for oral or parenteral administration. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as a pharmaceutically acceptable carrier include, but are not limited to, ion exchangers, alumina, aluminum stearate, lecithin, serum proteins, such as human serum albumin, buffer substances such as phosphates, carbonates, magnesium hydroxide and aluminum hydroxide, glycine, sorbic acid, or potassium sorbate, partial glyceride mixtures of saturated vegetable fatty acids, water, pyrogen-free water, salts or electrolytes such as protamine sulfate, disodium hydrogen phosphate, potassium hydrogen phosphate, sodium chloride, and zinc salts, colloidal silica, magnesium trisilicate, polyvinyl pyrrolidone, polyacrylates, waxes, polyethylene-polyoxypropylene-block polymers, wool fat; sugars such as lactose, glucose, sucrose, and mannitol; starches such as corn starch and potato starch, cellulose and its derivatives such as sodium carboxymethyl cellulose, ethyl cellulose and cellulose acetate, powdered tragacanth; malt, gelatin, talc; excipients such as cocoa butter and suppository waxes; oils such as peanut oil, cottonseed oil, safflower oil, sesame oil, olive oil, corn oil and soybean oil; glycols such as propylene glycol and polyethylene glycol; esters such as ethyl oleate and ethyl laurate; agar, alginic acid, isotonic saline, Ringer's solution, alcohols such as ethanol, isopropyl alcohol, hexadecyl alcohol, and glycerol; cyclodextrins such as hydroxypropyl p-cyclodextrin and sulfobutylether; beta-cyclodextrin; lubricants such as sodium lauryl sulfate and magnesium stearate; petroleum hydrocarbons such as mineral oil and petrolatum. In addition, coloring agents, releasing agents, coating agents, sweetening, flavoring and perfuming agents, preservatives and antioxidants can also be present in the composition, according to the judgment of the formulator.

The pharmaceutical composition of the invention is manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, emulsions, elixirs, suspensions or solutions.

When combined with a pharmaceutically acceptable carrier, the compound of the present invention is suited for administration orally, intravascularly, intraperitoneally, subcutaneously, intramuscularly, or topically using a liquid carrier form known to the pharmaceutical arts and as described below. Alternatively, the pharmaceutical composition of the present invention may be administered rectally or vaginally, in such forms as suppositories or bougies. In general, the preferred forms of the pharmaceutical composition are formulated for oral or intravenous administration, more typically for oral administration.

For the orally administered pharmaceutical compositions and methods of the present invention, the foregoing active compounds described herein are typically provided in admixture with suitable pharmaceutical diluents, excipients, or carriers (collectively referred to herein as "carrier" materials) suitably selected with respect to the intended mode and form of administration, that is, oral tablets, capsules, softgels, elixirs, syrups, drops, and the like, and consistent with well known pharmaceutical practices.

For example, for oral administration in the form of a tablet or capsule, a therapeutically effective amount of one or more compounds of the present invention are combined with any oral non-toxic pharmaceutically acceptable inert carrier such as lactose, starch, sucrose, cellulose, magnesium stearate, dicalcium phosphate, calcium sulfate mannitol, and the like, or various combinations thereof. For oral administration in liquid forms, such as in softgels, elixirs, syrups, drops and the like, a therapeutically effective amount of the active drug components is combined with any oral non-toxic pharmaceutically acceptable inert carrier such as water, saline, ethanol, polyethylene, glycol, propylene glycol, corn oil, cottonseed oil, peanut oil, sesame oil, benzyl alcohol, various buffers, and the like, or a combination thereof. When desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, or combinations thereof. Lubricants for use in these dosage forms include boric acid, sodium benzoate, sodium acetate, sodium chloride, and the like, or combinations thereof. Disintegrators include, without limitation, starch, methylcellulose, agar, bentonite, guar gum, and the like, or combinations thereof. Sweetening and flavoring agents and preservatives can also be included where appropriate.

For intravascular, intraperitoneal, subcutaneous, or intramuscular administration, one or more compounds of the present invention are combined with a suitable carrier such as water, isotonic saline, aqueous dextrose, and the like. For topical administration, one or more compounds of the present invention can be combined with pharmaceutically acceptable creams, oils, waxes, gels and the like. Regardless of the route of administration selected, the compounds of the present invention are formulated into pharmaceutically acceptable dosage forms by conventional methods known to those skilled in the art. The compounds may also be formulated using pharmacologically acceptable base addition salts. Moreover, the compounds or their salts may be used in a suitable hydrated form.

By virtue of their activity as APP2 antagonists, the compounds of Formula II are useful in inhibiting the breakdown of bradykinin (Bk), which in turn has the beneficial effects of dilating the arteries (such as the renal and coronary arteries as already discussed herein), reducing cardiac ischemia/reperfusion injury, stimulating the formation of new blood vessels, and increasing renal perfusion and function. As a result, the compounds of the present invention are useful as the active agent in a pharmaceutical composition for inhibiting the breakdown of bradykinin, for treating hypertension, for treating myocardial ischemia/reperfusion injury, or for enhancing renal function in a mammalian patient, preferably a human patient. A physician or veterinarian of ordinary skill can readily determine whether a patient exhibits hypertension, myocardial ischemia, or diminished renal function. The preferred utility relates to reducing ischemia/reperfusion injury in a mammalian patient.

By "mammalian patient" as used herein is meant a mammal in need of treatment such as a rat, mouse, horse, cow, pig, goat, sheep, or primate. Preferably, the mammalian patient is a primate. More preferably, the primate is a human.

Preferably, the pharmaceutical composition of the present invention is a compound of Formula II:
wherein $R_1$ is H, or; $R_3$—(CO)—
wherein $R_2$ is H; or alkyl having from 1 to 6 carbon atoms;
wherein $R_3$ is alkyl having from 1 to 6 carbon atoms;
or a pharmaceutically acceptable salt thereof.

More preferably, the pharmaceutical composition of the present invention is a compound of Formula II:
wherein $R_1$ is H; and
wherein $R_2$ is H; or alkyl having from 1 to 6 carbon atoms;
or a pharmaceutically acceptable salt thereof.

Most preferably, the pharmaceutical composition of the present invention is a compound of Formula II:
wherein $R_1$ is H; and $R_2$ is H;
or a pharmaceutically acceptable salt thereof. This compound is referred to herein as ST-115 and also is the compound of Formula III.

In its third aspect, the present invention is directed to a method for inhibiting bradykinin degradation in a mammalian patient, comprising administering to a mammalian patient in need of inhibition of bradykinin degradation a pharmaceutical composition comprising a pharmaceutically acceptable carrier, and a therapeutically effective amount of a compound of Formula II:

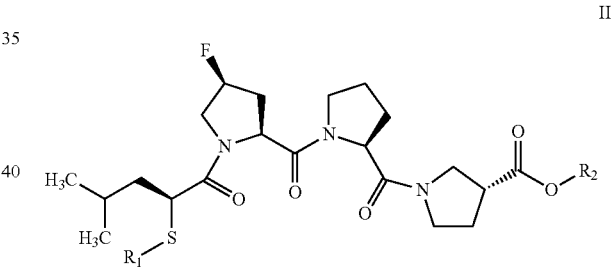

II wherein $R_1$ is H or

wherein $R_2$ is H; alkyl or substituted alkyl, having from 1 to 6 carbon atoms; or cycloalkyl-$(CH_2)_a$—, aryl-$(CH_2)_a$—, substituted aryl-$(CH_2)_a$—, or heteroaryl-$(CH_2)_a$—, having from 4 to 12 carbon atoms;
wherein $R_3$ is alkyl or substituted alkyl, having 1-6 carbon atoms; or cycloalkyl-$(CH_2)_a$—, aryl-$(CH_2)_a$—, substituted aryl-$(CH_2)_a$—, or heteroaryl-$(CH_2)_a$—, having from 4 to 12 carbon atoms; and
a is zero or an integer from 1 to 6;
or a pharmaceutically acceptable salt thereof.

Preferably, in the method of the present invention, the pharmaceutical composition is a compound of Formula II:
wherein $R_1$ is H, or; $R_3$—(CO)—
wherein $R_2$ is H; or alkyl having from 1 to 6 carbon atoms;
wherein $R_3$ is alkyl having from 1 to 6 carbon atoms;
or a pharmaceutically acceptable salt thereof.

More preferably, in the method of the present invention, the pharmaceutical composition is a compound of Formula II: wherein $R_1$ is H; and
wherein $R_2$ is H; or alkyl having from 1 to 6 carbon atoms; or a pharmaceutically acceptable salt thereof.

Most preferably, in the method of the present invention, the pharmaceutical composition is a compound of Formula II: wherein $R_1$ is H; and $R_2$ is H;
or a pharmaceutically acceptable salt thereof. This compound is referred to herein as ST-115 and also is the compound of Formula III.

In another embodiment, the method of inhibiting bradykinin degradation in the mammalian patient is associated with preventing or ameliorating reperfusion injury in the mammalian patient following an ischemic episode. Typically, in the above method, the tissue in the mammalian patient that is subject to the reperfusion injury following an ischemic episode is kidney, lung, liver, myocardium, brain, limb or the whole body following cardiac arrest. Preferably, the tissue is the kidney or the myocardium. More preferably, the tissue is the myocardium.

EXAMPLE 1

A. Preparation of [(S)-2-mercapto-4-methylpentanoyl]-4(S)-fluoro-Pro-Pro-[(3R)-β-Pro]-OH The above-titled compound of Formula III, [(S)-2-mercapto-4-methylpentanoyl]-4(S)-fluoro-Pro-Pro-[(3R)-β-Pro]-OH, was commercially prepared by CPC Scientific Inc., Sunnyvale Calif., USA as a contract synthesizer. A method for synthesis is described below.

B. Preparation of (R)-2-bromo-4-methylpentanoic acid

The (R)-2-amino-4-methylpentanoic acid (H-D-Leu-OH, 4 g, 30.5 mmol) was dissolved in a mixture of HBr 48% (9.6 mL, 84 mmol) and $H_2O$ (30 mL). At 0° C., a solution of $NaNO_2$ (2.62 g, 38 mmol) in $H_2O$ (15 mL) was added over a period of 60 min. The reaction was stirred for 1.5 hours at 0° C. and 1.5 hours at room temperature. The reaction mixture was degassed in vacuo and extracted with ethyl acetate (EtOAc) (3×50 mL). The extract was washed with water (50 mL), dried ($Na_2SO_4$), filtered and evaporated to give 4.52 g crude as oil. The oil was distillated at high vacuum to obtain 3.56 g of (R)-2-bromo-4-methylpentanoic acid as oil.

C. Preparation of (S)-2-acetylthio-4-methylpentanoic acid

The (R)-2-bromo-4-methylpentanoic acid (3.56 g, 18.3 mmol) was dissolved in 60 ml of dimethyl formamide (DMF), and a solution of $CH_3COSK$ (3.13 g, 27.4 mmol) in DMF (30 mL) was added at 0° C. under nitrogen atmosphere. The reaction mixture was stirred for 2 hours and then evaporated. The residue was redissolved in EtOAc (100 mL), washed with 5% potassium bisulfate (45 mL) and water (45 mL) and 1N HCl (45 mL) and brine (45 mL), dried ($Na_2SO_4$), and evaporated to obtain 3.2 g of the (S)-2-acetythio-4-methylpentanoic acid as a pale yellow oil.

D. Preparation of [(S)-2-acetylthio-4-methylpentanoyl]-4(S)-fluoro-Pro-Pro-[(3R)-β-Pro]-OH (Compound of Formula IV)

To H-4(S)-fluoro-Pro-Pro-[(3R)-β-Pro]-CTC-resin (2 mmol, obtained from CPC Scientific Inc., Sunnyvale, USA) in a reaction vessel with DMF (45 mL), (S)-2-acetylthio-4-methylpentanoic acid (1.15 g, 6 mmol), DIC (940 μL, 6 mmol), HOBt (810 mg, 6 mmol), and DIEA (1.04 mL, 6 mmol) were added. After shaking overnight at room temperature, the ninhydrin test showed coupling completed. The resin was washed with DMF (3×30 mL) and dichloromethane (3×30 mL), and then was cleaved with 1% trifluoroacetic acid/dichloromethane (TFA/DCM) (150 mL) for 1 hour at room temperature. The resin was removed by filtration under reduced pressure and washed with 1% TFA/DCM (50 mL). The filtrates were combined and concentrated to a glassy film on a rotary evaporator below 30° C. Cold diethyl ether (30 mL) was added to precipitate the peptide. The peptide was collected by filtration and washed with cold ether (2×5 mL). After drying, the crude titled peptide (670 mg) was obtained.

E. Preparation of [(S)-2-mercapto-4-methylpentanoyl]-4(S)-fluoro-Pro-Pro-[(3R)-β-Pro]-OH (Compound of Formula III)

The crude N-[(S)-2-acetylthio-4-methylpentanoyl]-4(S)-fluoro-Pro-Pro-[(3R)-13-Pro]-OH (670 mg) was dissolved in degassed tetrahydrofuran (THF) (50 mL), and 1N NaOH (10 mL) was added at 0° C. under $N_2$ atmosphere. The reaction mixture was stirred for 4 hours at room temperature. After acidification with 2 N HCl to pH 4, the solvent was evaporated. The residue (580 mg) was purified using preparative reverse phase HPLC with C-18 column, eluting with a water (containing 0.1% TFA)-acetonitrile gradient. The column fractions were analyzed by analytical HPLC and fractions containing product (purity >97%) were pooled to yield 185 mg of the titled peptide (Compound of Formula III) after lyophilization. Mass spectral analysis of this peptide revealed an $MS^+$ peak at 457.6 and $M+Na^+$ peak at 479.3.

EXAMPLE 2

A. Preparation of Highly Purified Human Aminopeptidase P2 from Kidney

Human kidney tissue, which was obtained from the Cooperative Human Tissue Network, was the source of purified human APP2 as used herein. APP2 enzyme activity was measured during purification as described in Example 2B below. The membrane-bound APP2 was purified from human kidney tissue using the following steps: 1) kidney tissue was homogenized in 30 volumes of buffer containing Triton X-100 detergent and centrifuged; 2) the pellet was washed and suspended in buffer containing octyl-β-D-glucopyranoside detergent, and then centrifuged; 3) the supernatant was treated with 10 units of phosphatidylinositol-specific phospholipase C (Invitrogen, Eugene, Ga.) to remove the hydrophobic part of the glycosyl-phosphatidylinositol lipid membrane anchor from APP2, and then dialyzed; 4) the dialysate was passed through an octyl-Sepharose chromatography column; 5) the eluent was centrifuged and then concentrated by ultrafiltration in Amicon Ultra-15 Ultracel-10 k filters (Millipore Corp, Billerica, Mass.); 6) the retentate was dialyzed and applied to a HiTrap Q-Sepharose XL ion exchange chromatography column. Human APP2 enzyme activity was eluted with a linear KCl salt gradient.

B. Determination of Human AAP2 Activity

Human aminopeptidase P2 (APP2) enzyme activity was determined using the internally quenched fluorescent substrate: H-Lys(2-aminobenzoyl)-Pro-Pro-p-nitroanilide (Bachem, Torrance, Calif.) at 1 μM ($=K_m$) for inhibitor studies and 5 μM for enzyme purification assays. The assay buffer was 0.1 M HEPES, pH 7.4, and the assay temperature was 30° C. Cleavage of the substrate by the enzyme produces an increase in fluorescence due to the release of H-Lys(2-aminobenzoyl). Enzyme rates were determined in an F. fluorescence plate reader (Molecular Devices, Sunnyvale, Calif.) using an excitation wavelength of 320 nm and an emission wavelength of 405 nm. The binding affinity of an inhibitor was estimated and expressed as $IC_{50}$ values (the concentration that inhibits activity by 50%).

EXAMPLE 3

Determination of Human ACE Activity

Human recombinant angiotensin-converting enzyme (hrACE) was obtained from R&D Systems (Minneapolis, Minn.). Its enzyme activity was determined using the internally quenched fluorescent substrate ES005: (7-methoxycoumarin-4-yl)acetyl-Arg-Pro-Pro-Gly-Phe-Ser-Ala-Phe-(2,4-dinitrophenyl)-Lys (R&D Systems, Minneapolis, Minn.). The assay buffer was 0.1 M HEPES, pH 7.4, and the temperature was 30° C. The substrate concentration was below $K_m$ (≤40 μM). Enzyme rates were determined in an $F_{max}$ fluorescence plate reader (Molecular Devices, Sunnyvale, Calif.) using an excitation wavelength of 320 nm and an emission wavelength of 405 nm. The binding affinity of an inhibitor was estimated and expressed as $IC_{50}$ values (the concentration that inhibits activity by 50%).

EXAMPLE 4

Bilateral Renal Ischemia/Reperfusion Protocols

Male CD-1(ICR) mice (36-47 g) from Harlan Laboratories (Indianapolis, Ind.) were used. Each mouse was anesthetized by the subcutaneous injection of 50 mg/kg sodium pentobarbital (Akorn Inc, Lake Forest, Ill.) and placed on a 37° C. warmer. For surgery, the abdomen was shaved and the mouse was moved to a warming plate with feedback temperature control (TCAT-2DF, Harvard Apparatus Holliston, Mass.). The body temperature of the mouse was maintained at 36.9±0.1° C. throughout the procedure. The skin of the abdomen was washed with alcohol, and a midline incision was made to expose the kidneys. After removing adipose tissue from the renal pedicles, a microaneurysm clamp was placed on each pedicle to block blood flow to/from both kidneys for 25 min. (referred to as the ischemia phase). At the 20 min. point, 0.15 ml of either saline or saline containing drug (apstatin or ST-115) was administered intravenously through the femoral vein. The doses were 1.8 mg/kg for apstatin and 10 μg/kg for ST-115. At 5 minutes after drug injection, the clamps were removed from the pedicles to restore blood flow to/from the kidneys (the reperfusion phase). After confirming reperfusion, a subcutaneous injection of saline was administered in the upper thigh for rehydration, and the incision was sutured closed. Regulated temperature control was maintained for at least the first 0.5 hours of reperfusion. The mouse was then placed on a 37° C. warmer to recover from the anesthetic and then moved to the home cage. After 2 days of reperfusion, the mouse was sacrificed by exsanguination. The blood was allowed to clot and then centrifuged to obtain serum. The serum was assayed for its concentration of urea (Blood Urea Nitrogen—BUN), a marker of kidney damage, using a kit from Stanbio (Boerne, Tex.). Mice were excluded from analysis if they had obvious infection or their kidneys failed to reperfuse completely (n=2). The BUN data points (20) were analyzed by comparing the values for each drug with those of the saline control using the unpaired t-test with Welch's correction (Graphpad Prism statistical package, La Jolla, Calif.). BUN values for mice that did not undergo the ischemia/reperfusion protocol were obtained to demonstrate "baseline" concentrations of urea.

What is claimed is:

1. A compound according to the formula:

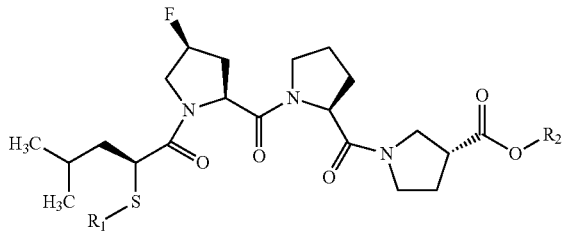

II wherein $R_1$ is H or $R_3$—(CO)—;
wherein $R_2$ is H; alkyl or substituted alkyl, having from 1 to 6 carbon atoms; or cycloalkyl-$(CH_2)_a$—, aryl-$(CH_2)_a$—, substituted aryl-$(CH_2)_a$—, or heteroaryl-$(CH_2)_a$—, having from 4 to 12 carbon atoms
wherein $R_3$ is alkyl or substituted alkyl, having 1-6 carbon atoms; or cycloalkyl-$(CH_2)_a$—, aryl-$(CH_2)_a$—, substituted aryl-$(CH_2)_a$—, or heteroaryl-$(CH_2)_a$—, having from 4 to 12 carbon atoms;
a is zero or an integer from 1 to 6; or
a pharmaceutically acceptable salt thereof.

2. The compound of claim 1, wherein $R_1$ is H.

3. The compound of claim 2, wherein $R_2$ is H or alkyl having from 1 to 6 carbon atoms.

4. The compound of claim 3, wherein $R_2$ is H.

5. The compound of claim 3, wherein $R_2$ is alkyl having from 1 to 4 carbon atoms.

6. The compound of claim 1, wherein $R_1$ is $R_3$—(CO)—.

7. The compound of claim 6, wherein $R_3$ is alkyl having from 1 to 6 carbon atoms.

8. The compound of claim 7, wherein $R_2$ is alkyl having from 1 to 6 carbon atoms.

9. A pharmaceutical composition comprising a pharmaceutically acceptable carrier and a therapeutically effective amount of a compound of Formula II,
wherein $R_1$ is H or $R_3$—(CO)—;
wherein $R_2$ is H; alkyl or substituted alkyl, having from 1 to 6 carbon atoms; or cycloalkyl-$(CH_2)_a$—, aryl-$(CH_2)_a$—, substituted aryl-$(CH_2)_a$—, or heteroaryl-$(CH_2)_a$—, having from 4 to 12 carbon atoms;
wherein $R_3$ is alkyl or substituted alkyl, having 1-6 carbon atoms; or cycloalkyl-$(CH_2)_a$—, aryl-$(CH_2)_a$—, substituted aryl-$(CH_2)_a$—, or heteroaryl-$(CH_2)_a$—, having from 4 to 12 carbon atoms;
a is zero or an integer from 1 to 6; or
a pharmaceutically acceptable salt thereof.

10. The pharmaceutical composition of claim 9, wherein $R_1$ is H.

11. The pharmaceutical composition of claim 10, wherein $R_2$ is H or alkyl having from 1 to 6 carbon atoms.

12. The pharmaceutical composition of claim 11, wherein $R_2$ is H.

13. The pharmaceutical composition of claim 11, wherein $R_2$ is alkyl having from 1 to 4 carbon atoms.

14. The pharmaceutical composition of claim 9, wherein $R_1$ is $R_3$—(CO)—.

15. The pharmaceutical composition of claim 14, wherein $R_3$ is alkyl having from 1 to 6 carbon atoms.

16. The pharmaceutical composition of claim 15, wherein $R_2$ is alkyl having from 1 to 6 carbon atoms.

17. A method for inhibiting bradykinin degradation in a mammalian patient comprising: administering to a mammalian patient in need of inhibition of bradykinin degradation a pharmaceutical composition comprising a pharmaceutically acceptable carrier, and a therapeutically effective amount of a compound of Formula II:

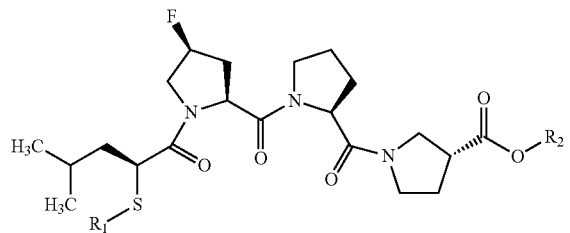

wherein $R_1$ is H or

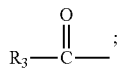

wherein $R_2$ is H; alkyl or substituted alkyl, having from 1 to 6 carbon atoms; or cycloalkyl-$(CH_2)_a$—, aryl-$(CH_2)_a$—, substituted aryl-$(CH_2)_a$—, or heteroaryl-$(CH_2)_a$—, having from 4 to 12 carbon atoms;

wherein $R_3$ is alkyl or substituted alkyl, having 1-6 carbon atoms; or cycloalkyl-$(CH_2)_a$—, aryl-$(CH_2)_a$—, substituted aryl-$(CH_2)_a$—, or heteroaryl-$(CH_2)_a$—, having from 4 to 12 carbon atoms; and a is zero or an integer from 1 to 6; or a pharmaceutically acceptable salt thereof.

18. The method of claim 17, wherein said inhibiting bradykinin degradation in a mammalian patient is associated with preventing or ameliorating reperfusion injury in said mammalian patient.

19. The method of claim 18, wherein $R_2$ is H or alkyl having from 1 to 6 carbon atoms.

20. The method of claim 19, wherein $R_1$ is H.

* * * * *

UNITED STATES PATENT AND TRADEMARK OFFICE
CERTIFICATE OF CORRECTION

PATENT NO.        : 9,212,206 B1
APPLICATION NO.   : 14/544096
DATED             : December 15, 2015
INVENTOR(S)       : William H. Simmons Page 1 of 1

It is certified that error appears in the above-identified patent and that said Letters Patent is hereby corrected as shown below:

On the Title Page, item 56, column 2, line 5, the word "Cpmorbities" should read --Comorbidities--, In the specification Column 1, line 29, the word "Comorbities" should read --Comorbidities--, Column 1, lines 39-40, the word "ischemiareperfusion" should read --ischemia/reperfusion--, Column 8, line 47, "(nM/L)" should read --(nmol/L)-- and "AAP2" should read --APP2--, Column 8, lines 48-49 and 51, each "ACE/AAP2" should read --ACE/APP2--, Column 9, lines 36 and 40, each "ACE/AAP2" should read --ACE/APP2--, Column 17, line 2, "F." should read --$F_{max}$--.

Signed and Sealed this
Twenty-eighth Day of June, 2016

Michelle K. Lee
*Director of the United States Patent and Trademark Office*